United States Patent
Kohori et al.

(10) Patent No.: US 8,524,309 B2
(45) Date of Patent: Sep. 3, 2013

(54) OIL OR FAT COMPOSITION

(71) Applicant: Kao Corporation, Tokyo (JP)

(72) Inventors: Jun Kohori, Tokyo (JP); Masao Shimizu, Tokyo (JP); Shin Koike, Tokyo (JP); Keiji Shibata, Kamisu (JP); Hiroaki Yamaguchi, Kamisu (JP); Minoru Kase, Kamisu (JP); Yoshitaka Senda, Kamisu (JP); Manabu Sato, Kamisu (JP); Eizo Maruyama, Kamisu (JP); Hidenari Imai, Tokyo (JP); Tsutomu Nishide, Kamisu (JP); Nobuteru Ishizuka, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/724,373

(22) Filed: Dec. 21, 2012

(65) Prior Publication Data

US 2013/0189394 A1 Jul. 25, 2013

Related U.S. Application Data

(62) Division of application No. 11/579,148, filed as application No. PCT/JP2005/006186 on Mar. 30, 2005, now abandoned.

(30) Foreign Application Priority Data

| Apr. 28, 2004 | (JP) | 2004-134749 |
| Jun. 10, 2004 | (JP) | 2004-172102 |
| Oct. 8, 2004 | (JP) | 2004-295634 |
| Oct. 15, 2004 | (JP) | 2004-302271 |

(51) Int. Cl.
*A23D 9/007* (2006.01)

(52) U.S. Cl.
USPC .......................... 426/601; 426/611

(58) Field of Classification Search
USPC ................................ 426/601–611
See application file for complete search history.

(56) References Cited

U.S. PATENT DOCUMENTS

| 4,656,045 | A | 4/1987 | Bodor et al. | |
| 4,913,921 | A | 4/1990 | Schroeder et al. | |
| 4,976,984 | A | 12/1990 | Yasukawa et al. | |
| 6,106,879 | A | 8/2000 | Mori et al. | |
| 6,139,897 | A | 10/2000 | Goto et al. | |
| 6,326,050 | B1 | 12/2001 | Goto et al. | |
| 6,495,536 | B1 | 12/2002 | Masui et al. | |
| 6,713,118 | B2 | 3/2004 | Nakajima et al. | |
| 6,753,032 | B1 | 6/2004 | Hirokawa et al. | |
| 7,182,971 | B2 * | 2/2007 | Takase et al. | 426/601 |
| 8,227,010 | B2 * | 7/2012 | Kase et al. | 426/601 |
| 2002/0142089 | A1 | 10/2002 | Koike et al. | |
| 2003/0198727 | A1 | 10/2003 | Koike et al. | |
| 2005/0054621 | A1 | 3/2005 | Gako-Golan et al. | |

FOREIGN PATENT DOCUMENTS

| CN | 1370050 A | 9/2002 |
| EP | 0679712 | 11/1995 |
| IL | 03/064444 | 8/2003 |
| JP | 61-63242 | 4/1986 |
| JP | 02-190146 | 7/1990 |
| JP | 03-008431 | 1/1991 |
| JP | 04-300826 | 10/1992 |
| JP | 10-176181 | 6/1998 |
| JP | 11-243857 | 9/1999 |
| JP | 2001-64671 | 3/2001 |
| JP | 2001-211828 | 8/2001 |
| JP | 2001-294891 | 10/2001 |
| JP | 2001-335795 | 12/2001 |
| JP | 2002-034453 | 2/2002 |
| JP | 2002-053892 | 2/2002 |
| JP | EP1180545 | 2/2002 |
| JP | 2002-138296 | 5/2002 |
| JP | 2002-138297 | 5/2002 |
| JP | 2002-171931 | 6/2002 |
| JP | 2002-206100 | 7/2002 |
| WO | 96/06605 | 3/1996 |
| WO | 96/32022 | 10/1996 |
| WO | 98/37873 | 9/1998 |
| WO | 99/48378 | 9/1999 |
| WO | 00/73407 | 12/2000 |
| WO | 01/10989 | 2/2001 |
| WO | 02/11552 | 2/2002 |
| WO | WO 03/024237 A1 | 3/2003 |

OTHER PUBLICATIONS

Office Action issued May 9, 2011, in Taiwanese Patent Application No. 094110365.

Alice H. Lichtenstein, et al., "Effects of different forms of dietary hydrogenated fats on serum lipoprotein cholesterol levels", The New England Journal of Medicine, vol. 340, No. 25, Jun. 24, 1999, pp. 1933-1940.

Hui, Y.H. 1996, Bailey's Industrial Oil and Fat Products, $5^{th}$ edition, vol. 2, John Wiley & Sons, Inc., New York p. 45, 46, 256, 501.

Swern, D. 1979, Bailey's Industrial Oil and Fat Products, $4^{th}$ edition, vol. 1, John Wiley & Sons, New York, p. 428-429.

US 5,670,348, 09/1997, Cain et al. (withdrawn)

* cited by examiner

Primary Examiner — Carolyn Paden

(74) Attorney, Agent, or Firm — Oblon, Spivak, McClelland, Maier & Neustadt, L.L.P.

(57) ABSTRACT

Provided is an oil or fat composition of high diacylglycerol content. Even when used in cooking, the cooked food has a good external appearance without darkening, and retains its inherent flavor. Even when used in cooking after storage under light-exposed conditions, the cooked food is provided with a good external appearance and flavor.

The oil or fat composition is obtained by combining, at specific contents, (A) an oil or fat of high diacylglycerol content, said oil or fat having a particular composition, (B) a plant sterol and (C) a plant sterol fatty acid ester.

16 Claims, No Drawings

OIL OR FAT COMPOSITION

CROSS REFERENCES TO RELATED APPLICATIONS

This application is a Divisional Application of U.S. patent application Ser. No. 11/579,148, filed on Oct. 30, 2006, which was a 371 of International Patent Application No. PCT/JP05/06186, filed on Mar. 30, 2005, and claims priority to Japanese Patent Application No. 2004-134749, filed on Apr. 28, 2004, Japanese Patent Application No. 2004-172102, filed on Jun. 10, 2004, Japanese Patent Application No. 2004-295634, filed on Oct. 8, 2004, and Japanese Patent Application No. 2004-302271, filed on Oct. 15, 2004.

FIELD OF THE INVENTION

This invention relates to oil or fat compositions of high diacylglycerol content.

BACKGROUND OF THE INVENTION

With the worldwide tendency toward a healthier lifestyle, a number of researches have been conducted about the functions of fatty acids in oil or fat. For example, there are reports about the effects of saturated fatty acids or trans unsaturated fatty acids on health (see Non-patent Documents 1 and 2).

Also, conjugated linoleic acid and diacylglycerol have been found to have an anti-obesity effect or the like (see Patent Documents 1 to 5). Further, oils or fats with diacylglycerol having a high content of a specific fatty acid such as an ω-3 fatty acid or linoleic acid are known (see Patent Documents 6 to 8).

In addition, it is known to combine diacylglycerol with a plant sterol, thereby improving the blood cholesterol level or the like (see Patent Documents 9 to 14).

The use of diacylglycerol as a cooking oil is known to have some advantages, such as less occurrence of substantial foaming during frying, and an increase in the improvement of flavor and texture (see Patent Documents 15 and 16). Diacylglycerols have also been proven to be applicable to emulsified products (see Patent Documents 17-19). From these viewpoints, oil or fat compositions of high diacylglycerol content are widely used as edible oils.

Patent Document 1: PCT International Publication Pamphlet No. WO 96/06605
Patent Document 2: PCT International Publication Pamphlet No. WO 98/37873
Patent Document 3: JP-A-04-300826
Patent Document 4: JP-A-10-176181
Patent Document 5: JP-A-2001-64671
Patent Document 6: PCT International Publication Pamphlet No. WO 01/109899
Patent Document 7: PCT International Publication Pamphlet No. WO 02/11552
Patent Document 8: EP-A-0679712
Patent Document 9: PCT International Publication Pamphlet No. WO 99/48378
Patent Document 10: JP-A-2002-34453
Patent Document 11: PCT International Publication Pamphlet No. WO 00/73407
Patent Document 12: JP-A-2000-206100
Patent Document 13: JP-A-2002-171931
Patent Document 14: JP-A-2001-335795
Patent Document 15: JP-A-11-243857
Patent Document 16: JP-A-02-190146
Patent Document 17: JP-B-1915615
Patent Document 18: PCT International Publication Pamphlet No. WO 96/32022
Patent Document 19: JP-A-03-8431
Non-patent Document 1: "The New England Journal of Medicine", USA, the Massachusetts Medical Society, 340 (25), 1933-1940 (1999)
Non-patent Document 2: U.S. FDA, "Questions and Answers about Trans Fat Nutrition Labeling", [online], Internet <URL: http://www.cfsan.fda.gov/~dms/qatrans2.html>

SUMMARY OF THE INVENTION

It has now come to light that in some cases, the conventional oil or fat compositions of high diacylglycerol content are not necessarily fully satisfactory in respects of the external appearance and flavor needed for a cooked food, influenced by their storage conditions and cooking conditions. More specifically, a food cooked with an oil or fat composition of high diacylglycerol content has been found to have susceptibility to dullness and impairment in its external appearance, as well as to deterioration of its inherent favorable flavor, depending upon how it is used during cooking. It has also been found that the above-mentioned tendency becomes prominent especially when the oil or fat composition is stored under light-exposed conditions prior to its cooking.

By an investigation made by the present inventors, it has been revealed that conjugated unsaturated fatty acids, trans unsaturated fatty acids, a plant sterol and a plant sterol fatty acid ester in a diacylglycerol-containing oil or fat are implicated in the above-described problems, so that such problems are resolved if their contents are adjusted to certain particular ranges.

The present invention provides an oil or fat composition containing the following ingredients (A), (B) and (C):

(A) 100 weight parts of an oil or fat containing 15 wt % or more of diacylglycerol, in constituent fatty acids of which a content of unsaturated fatty acids is 80 wt % or more, wherein in whole fatty acids that constitute the oil or fat, a content of conjugated unsaturated fatty acids is 1 wt % or less and a content of trans unsaturated fatty acids is 4 wt % or less;

(B) from 0.01 to 4.7 weight parts of a plant sterol; and (C) from 0.2 to 8 weight parts of a plant sterol fatty acid ester.

DETAILED DESCRIPTION OF THE INVENTION

According to the present invention, even when cooked while using the invention oil or fat composition of high diacylglycerol content, for example, the resultant cooked food or product is free of dullness, has a good external appearance, and retains its inherent flavor. Further, even when cooked with the invention oil or fat composition of high diacylglycerol content after its storage under light-exposed conditions, for example, the resultant cooked food or product is provided with a good external appearance and flavor.

The individual ingredients of the above-described composition, that is, the oil or fat (A), the plant sterol (B) and the plant sterol fatty acid ester (C) are hereinafter described in detail. A description is also made of preferred or recommended embodiments of the raw material and production process of the oil or fat (A), an antioxidant (D) and a crystallization inhibitor (E). Further, a description is also made of preferred or recommended embodiments on the application of the composition according to the present invention to foods, medicines and feeds. In addition, a series of nonlimiting examples are presented concerning some compositions according to the present invention.

In an embodiment of the present invention, the oil or fat (A) useful in the oil or fat composition contains 15 wt % (hereinafter shown simply by "%") or more of diacylglycerol (DG). From the stand points of physiological effects, industrial oil/fat productivity and external appearance, the oil or fat (A) may contain preferably from 15 to 95%, more preferably from 35 to 95%, even more preferably from 50 to 95%, even more preferably from 70 to 93%, even more preferably from 75 to 93%, yet even more preferably from 80 to 90% of DG. The carbon number of the unsaturated fatty acid is preferably 14-24, more preferably 16-22.

In another embodiment of the present invention, the diacylglycerol contained in the oil or fat (A) contains unsaturated fatty acids (UFA) as much as from 80 to 100% based on its constituent fatty acids. From the standpoints of external appearance, physiological effects and industrial oil/fat productivity, however, the constituent fatty acids may contain preferably from 90 to 100%, more preferably from 93 to 100%, even more preferably from 93 to 98%, even more preferably from 94 to 98% of UFA.

It is desired from the standpoints of external appearance and balanced fatty-acid ingestion that, in the fatty acids that constitute the diacylglycerol, the content of oleic acid ranges from 20 to 65%, preferably from 25 to 60%, more preferably from 30 to 50%, even more preferably from 30 to 45%. From the standpoints of external appearance and physiological effects, the content of dioleylglycerol in the diacylglycerols may be preferably 45% or less, more preferably from 0 to 40%.

From the standpoints of external appearance and balanced fatty-acid ingestion, the content of linoleic acid in fatty acids that constitute the diacylglycerol is desired to range preferably from 15 to 65%, more preferably from 20 to 60%, even more preferably from 30 to 55%, even more preferably from 35 to 50%. It is also desired from the standpoints of oxidation stability and physiological effects that the content weight ratio of linoleic acid to oleic acid in the diacylglycerol ranges from 0.01 to 2.0, preferably from 0.1 to 1.8, more preferably from 0.3 to 1.7.

From the standpoints of external appearance, balanced fatty-acid ingestion and oxidation stability, the content of linolenic acid in the fatty acids that constitute the diacylglycerol may desirably be 15% or less, preferably from 0 to 13%, more preferably from 1 to 10%, even more preferably from 2 to 9%. Although linolenic acid is known to include α-linolenic acid and 7-linolenic acid, α-linolenic acid is preferred.

In the fatty acids that constitute the diacylglycerol, the content of saturated fatty acids (SFA) may be less than 20%, preferably from 0 to 10%, more preferably from 0 to 7%, even more preferably from 2 to 7%, even more preferably from 2 to 6% from the standpoints of external appearance, physiological effects and industrial oil/fat productivity. As the saturated fatty acids, those having carbon numbers of from 14 to 24, desirably from 16 to 22 are preferred, with palmitic acid and stearic acid being more preferred.

In the fatty acids that constitute the diacylglycerol, the content of trans unsaturated fatty acids may be preferably from 0 to 4%, more preferably from 0.1 to 3.5%, even more preferably from 0.2 to 3% from the standpoints of flavor, physiological effects, external appearance and industrial oil/fat productivity.

In the fatty acids that constitute the diacylglycerol, the content of conjugated unsaturated fatty acids is 1% or less. From the standpoints of flavor, physiological effects, external appearance and industrial oil/fat productivity, however, the content of the conjugated unsaturated fatty acids may range preferably from 0.01 to 0.9%, more preferably from 0.1 to 0.8%, even more preferably from 0.2 to 0.75%, even more preferably from 0.3 to 0.7%.

In the fatty acids that constitute the diacylglycerol, the content of fatty acids having carbon numbers of 12 or less may be preferably 5% or less, more preferably from 0 to 2%, even more preferably from 0 to 1% from the standpoint of flavor, and even more preferably, the fatty acids are substantially free of those having carbon numbers of 12 or less. The remaining constituent fatty acids may be those having carbon numbers of preferably from 14 to 24, more preferably from 16 to 22.

From the standpoints of physiological effects, storage stability, industrial oil/fat productivity, and flavor, the percentage of a 1,3-diacylglycerol in the diacylglycerol may be preferably 50% or more, more preferably from 52 to 100%, even more preferably from 54 to 90%, even more preferably from 56 to 80%.

In a further embodiment of the present invention, it is desired from the standpoints of physiological effects, industrial oil/fat productivity, and external appearance that the oil or fat (A) useful in the oil or fat composition contains preferably from 4.9 to 84.9%, more preferably from 4.9 to 64.9%, even more preferably from 6.9 to 39.9%, even more preferably from 6.9 to 29.9%, even more preferably from 9.8 to 19.8% of a triacylglycerol (TG).

In a still further embodiment of the present invention, the constituent fatty acids of the triacylglycerol contained in the oil or fat (A) may preferably be the same as the constituent fatty acids of the diacylglycerol from the standpoints of physiological effects and industrial oil/fat productivity.

In a still further embodiment of the present invention, the constituent fatty acids of the triacylglycerol contained in the oil or fat (A) may contain preferably from 80 to 100%, more preferably from 90 to 100%, even more preferably from 93 to 100%, even more preferably from 93 to 98%, even more preferably from 94 to 98% of unsaturated fatty acids from the standpoints of physiological effects and industrial oil/fat productivity. The carbon numbers of the unsaturated fatty acids may range preferably from 10 to 24, more preferably from 16 to 22 from the standpoints of physiological effects and industrial oil/fat productivity.

In a still further embodiment of the present invention, the oil or fat (A) useful in the oil or fat composition may contain preferably from 0.1 to 5%, more preferably from 0.1 to 2%, even more preferably from 0.1 to 1.5%, even more preferably from 0.1 to 1.3%, even more preferably from 0.2 to 1% of a monoacylglycerol (MG) from the standpoints of flavor, external appearance, smoking, and industrial oil/fat productivity. A content of the monoacylglycerol not less than 0.1% is preferred in that the oil or fat may be readily heated when used in microwave oven cooking. From the standpoint of safety such as smoking during microwave oven cooking, however, 5% or less is preferred. The constituent fatty acids of the monoacylglycerol may preferably be the same as the constituent fatty acids of the diacylglycerol from the standpoint of industrial oil/fat productivity.

In a still further embodiment of the present invention, the content of free fatty acids or salts thereof (FFA) in the oil or fat (A) may be reduced to preferably 5% or less, more preferably from 0 to 3.5%, even more preferably from 0 to 2%, even more preferably from 0.01 to 1%, even more preferably from 0.05 to 0.5% from the standpoints of flavor, the prevention of smoking, and industrial oil/fat productivity.

In a still further embodiment of the present invention, the content of fatty acids, each of which contains four or more carbon-carbon double bonds, in the whole fatty acids that constitute the oil or fat (A) may preferably be from 0 to 40%, more preferably from 0 to 20%, even more preferably from 0 to 10%, even more preferably from 0 to 1%, and even more preferably, the whole fatty acids are substantially free of such fatty acids, from the standpoints of oxidation stability, work comfort, physiological effects, coloring, flavor and the like.

In a still further embodiment of the present invention, the content of trans unsaturated fatty acids in the whole fatty acids that constitute the oil or fat (A) is from 0 to 4%. From the standpoints of flavor, physiological effects, external appearance and industrial oil/fat productivity, however, the content of the trans unsaturated fatty acids may be preferably from 0.1 to 3.5%, more preferably from 0.2 to 3%.

In the present invention, the trans unsaturated fatty acid is a value as measured by the AOCS method (American Oil Chem. Soc. Official Method: Celf-96, 2002).

In a still further embodiment of the present invention, the content of conjugated unsaturated fatty acids in the whole fatty acids that constitute the oil or fat (A) is 1% or less. From the standpoints of flavor, physiological effects, external appearance and industrial oil/fat productivity, however, the content of the conjugated unsaturated fatty acids may be preferably from 0.01 to 0.9%, more preferably from 0.1 to 0.8%, even more preferably from 0.2 to 0.75%, even more preferably from 0.3 to 0.7%. In the conjugated unsaturated fatty acids, the content of a conjugated diene unsaturated fatty acid may be preferably 0.85% or less, more preferably from 0.01 to 0.8%, even more preferably from 0.1 to 0.75%, even more preferably from 0.2 to 0.7% from the standpoints of flavor and industrial oil/fat productivity. In the conjugated unsaturated fatty acids, the content of a conjugated triene unsaturated fatty acid may be preferably 0.1% or less, more preferably from 0.001 to 0.09%, even more preferably from 0.002 to 0.05%, even more preferably from 0.005 to 0.02% from the standpoints of flavor and industrial oil/fat productivity. A conjugated tetraene unsaturated fatty acid and conjugated pentaene unsaturated fatty acid may each be preferably 0.05% or less, more preferably from 0 to 0.01%, even more preferably from 0 to 0.005%, even more preferably 0.

In the present invention, each content of conjugated unsaturated fatty acid(s) is a value as quantitated in accordance with Standard Methods for the Analysis of Fats, Oils, and Related Materials, "Conjugated Unsaturated Fatty Acids (spectral method) 2.4.3-1996" (compiled by The Japan Oil Chemists' Society).

In a still further embodiment of the present invention, a source of the oil or fat (A) may be either a vegetable or animal oil or fat. Specific sources may include rapeseed oil, sunflower oil, corn oil, soybean oil, linseed oil, rice oil, safflower oil, cottonseed oil, beef tallow, and fish oil and the like. These oils and fats may also be used as sources after adjusting their fatty acid compositions by fractionation, blending, hydrogenation, transesterification or the like. Unhydrogenated oils or fats are, however, preferred from the standpoint of lowering the content of trans unsaturated fatty acids in the whole fatty acids that constitute the oil or fat (A). Vegetable oils of high unsaturated fatty acid content are preferred, with rapeseed oil and soybean oil being more preferred, in that physiological effects are improved and products are provided with a good external appearance without becoming turbid.

In a still further embodiment of the present invention, it is preferred to remove solids other than an oil or fat component by filtration, centrifugation or the like after an oil or fat material is collected by mechanical expression from the corresponding vegetable or animal source. Preferably, degumming may then be conducted by eliminating a gum component by centrifugation or the like after the addition and mixing of water and optionally, also an acid. It is also preferred to conduct refining by washing the oil or fat material with water subsequent to the addition and mixing of an alkali. It is also preferred to conduct bleaching by bringing the oil or fat material into contact with an adsorbent such as activated clay and then removing the adsorbent by filtration or the like. These treatments may preferably be conducted in this order, although their order may be changed. For the elimination of wax components, the oil or fat material may also be subjected to wintering that removes solid components at low temperature. It is also preferred to conduct deodorization by bringing the oil or fat material into contact with steam under reduced pressure. From the standpoint of lowering the content of trans unsaturated fatty acids and conjugated unsaturated fatty acids in the oil or fat, it is preferred to limit the thermal history as much as possible upon conducting the deodorization. As conditions for the deodorization step, it is preferred for the same reasons as mentioned above to control the temperature at 300° C. or lower, preferably at 270° C. or lower and to limit the time to 10 hours or shorter, preferably 5 hours or shorter.

As the oil or fat material, an undeodorized oil or fat not subjected to deodorization in advance may also be used instead of a deodorized oil or fat. In the present invention, it is preferred to use an undeodorized oil as a part or the whole part of the raw material because the content of trans unsaturated fatty acids and conjugated unsaturated fatty acids may be lowered in the oil or fat, and plant sterols, plant sterol fatty acid esters and tocopherol (Toc) which have been derived from the oil or fat material, are allowed to remain in the oil or fat composition.

In a still further embodiment of the present invention, the oil or fat (A) may be obtained by transesterification between fatty acids derived from the above-mentioned oil or fat and glycerol, transesterification between such an oil or fat and glycerol, or a like reaction. Excess monoacylglycerols formed by the reaction may be eliminated by molecular distillation or chromatography. It is preferred from the standpoints of flavor and the like to conduct these reactions with 1,3-selective lipase or the like under enzymatic mild conditions, although the reactions may also be conducted as chemical reactions by making use of an alkali catalyst or the like.

In a still further embodiment of the present invention, the fatty acids that constitute the oil or fat (A) may be produced by hydrolyzing the oil or fat material. The hydrolysis of the oil or fat material may be conducted by high-pressure hydrolysis and enzymatic hydrolysis. In the above step, it is preferred to hydrolyze a part or the whole part of the oil or fat material by enzymatic hydrolysis of limited thermal history because the contents of trans unsaturated fatty acids and conjugated unsaturated fatty acids are lowered in the oil or fat, and because the content of plant sterols and plant sterol fatty acid esters, which have been derived from the oil or fat material, remains. When an objective is only to lower the content of trans unsaturated fatty acids in the oil or fat, it is preferred to hydrolyze the oil or fat material in its entirety by enzymatic hydrolysis of limited thermal history. From the standpoint of providing the oil or fat with a high-quality flavor and color and also from the standpoint of industrial oil/fat productivity, however, the percentage of the oil or fat material which is to be hydrolyzed by high-pressure hydrolysis may be set at preferably 30% or more, more preferably from 35 to 95%, even more preferably from 40 to 90%.

As a method for conducting hydrolysis by combining high-pressure hydrolysis and enzymatic hydrolysis in the hydrolysis of the oil or fat material, it is possible not only to hydrolyze a part of the oil or fat material by high-pressure hydrolysis and the remaining part of the oil or fat material by enzymatic hydrolysis but also (x) to hydrolyze the whole oil or fat material partway by high-pressure hydrolysis and then to conduct the hydrolysis by enzymatic hydrolysis, (y) to hydrolyze the whole oil or fat material partway by enzymatic hydrolysis and then to conduct the hydrolysis by high-pressure hydrolysis, or (z) to conduct the hydrolysis of a part of the oil or fat material by the method (x) and the hydrolysis of the remaining part of the oil or fat material by the method (y).

The color of the oil or fat material was measured in accordance with American Oil Chemists' Society Official Method Cc 13e-92 (Lovibond method). From the standpoint of the quality (flavor, color) of the final product, the color C of the oil or fat material as defined by the below-described formula (1) is preferably 30 or less, more preferably from 1 to 25, even more preferably from 5 to 20.

Formula (1)

$$C=10R+Y \qquad (1)$$

In the measurement, a 133.4 mm cell is used. A red value is represented by R, a yellow value is represented by Y, and C is a value (10R+Y) obtained by adding a 10-fold value of the red value and the yellow value together.

In a still further embodiment of the present invention, it is preferred to conduct the hydrolysis by high-pressure hydrolysis when the color of the oil or fat material after the deodorization step does not meet the above-described conditions or to conduct the hydrolysis by enzymatic hydrolysis when the color of the oil or fat material after the deodorization step meets the above-described conditions, because the final product is provided with a good color, is lowered in the content of trans unsaturated fatty acids, and is provided with high quality.

When trans unsaturated fatty acids are already high in the fatty acids that constitute the oil or fat material, it is preferred to conduct the hydrolysis of the oil or fat material by enzymatic hydrolysis, because the use of enzymatic hydrolysis minimizes an increase in the contents of trans unsaturated fatty acids and conjugated unsaturated fatty acids in the fatty acids or an oil or fat to be obtained. When trans unsaturated fatty acids are low in the fatty acids that constitute the oil or fat material, on the other hand, it is preferred to conduct the hydrolysis of the oil or fat material by high-pressure hydrolysis from the standpoints of the efficiency of the step and the flavor and color of the oil or fat. As the oil or fat material to be subjected to hydrolysis by high-pressure hydrolysis, the content of trans unsaturated fatty acids in the fatty acids that constitute the oil or fat material may be preferably 1% or less, more preferably from 0.01 to 0.8%, even more preferably from 0.1 to 0.5%. When hydrolysis is conducted by combining high-pressure hydrolysis and enzymatic hydrolysis, the content of trans unsaturated fatty acids in the whole oil or fat material may be preferably 1.5% or less, more preferably 1% or less, even more preferably 0.5% or less from the standpoint of lowering the content of trans unsaturated fatty acids in the final product. It is to be noted that, when two or more oils or fats are used, the content of trans unsaturated fatty acids means their content in the sum of the oils or fats.

The higher the degree of unsaturation of the constituent fatty acids in the oil or fat material, the easier the occurrence of transisomerization by heating. In the case of an oil or fat abundantly containing fatty acids of high unsaturation degree, it is therefore preferred to conduct its hydrolysis by enzymatic hydrolysis. Specifically, substantially no transisomerization takes place by heating in the case of oleic acid the degree of unsaturation of which is 1, whereas transisomerization becomes pronounced in the case of a fatty acid the degree of unsaturation of which is 2 or higher, for example, linoleic acid or linolenic acid. As an oil or fat material to be subjected to hydrolysis by enzymatic hydrolysis, the content of fatty acids, the degrees of unsaturation of which are not less than 2, in the fatty acids that constitute the oil or fat material may therefore be preferably 40% or more, more preferably from 50 to 100%, even more preferably from 60 to 90%. The higher the degree of unsaturation, the more pronounced the transisomerization. In the case of an oil or fat material containing 10% or more of fatty acids the degrees of unsaturation of which are not less than 3, it is therefore preferred to conduct its hydrolysis by enzymatic hydrolysis.

In a still further embodiment of the present invention, the oil or fat material may be hydrolyzed for from 2 to 6 hours with high-pressure hot water of from 220 to 270° C. by the high-pressure hydrolysis method. From the standpoints of industrial oil/fat productivity and the inhibition of coloring and the formation of trans unsaturated fatty acids and conjugated unsaturated fatty acids, however, the temperature of the high-pressure hot water may be set preferably at from 225 to 265° C., more preferably at from 230 to 260° C. From a similar standpoint, the time may be limited preferably to from 2 to 5 hours, more preferably to from 2 to 4 hours.

In a still further embodiment of the present invention, lipase is preferred as an oil/fat-splitting enzyme to be used in the enzymatic hydrolysis. As lipase, commercial lipase derived from a microorganism may be used, to say nothing of one derived from an animal or plant.

In a still further embodiment of the present invention, the esterification process of fatty acids and glycerol may be either a chemical synthesis process or an enzymatic process. The use of an enzymatic process is, however, preferred in that the content of trans unsaturated fatty acids in the final oil or fat product is not increased.

In a still further embodiment of the present invention, it is preferred to employ lipase as an enzyme for use in the esterification. Especially when the objective is to produce a functional oil or fat such as diacylglycerol, examples include those capable of readily and selectively synthesizing the diacylglycerol such as *Rhizopus, Aspergillus, Mucor, Pseudomonas, Geotrichum, Penicillium*, and *Candida*.

As an enzyme for use in the esterification, it is preferred to employ an immobilized one from the standpoint of cost.

In a still further embodiment of the present invention, the glycerols produced by conducting the esterification may be formed into a final product by conducting post-treatment. As the post-treatment, it is preferred to conduct refining (elimination of unreacted fatty acids), acid treatment, water washing, and deodorization. The deodorization, temperature may preferably be from 200 to 280° C. The deodorization time may preferably be from 2 minutes to 2 hours. The pressure at the time of the deodorization may preferably be from 0.01 to 5 kPa. The volume of steam at the time of the deodorization may preferably be from 0.1 to 10% based on the oil or fat material.

In a still further embodiment of the present invention, the oil or fat composition is required to contain the plant sterol (B). The term "plant sterol" as used herein means, different from the ingredient (C), one in which the hydroxyl group is not ester-bonded with a fatty acid but is in its free form (free sterol). In a still further embodiment of the present invention, the content of the ingredient (B) is from 0.01 to 4.7 weight parts per 100 weight parts of the oil or fat (A). From the standpoints of flavor, external appearance and industrial oil/fat productivity, however, the content of the ingredient (B) may be preferably from 0.02 to 4.6 weight parts, more preferably from 0.03 to 4.5 weight parts, even more preferably from 0.05 to 4.4 weight parts, even more preferably from 0.1 to 4.3 weight parts.

When desired to allow a vegetable-oil-derived sterol to remain as the plant sterol (B), its content may be preferably from 0.01 to 1.0 weight parts, more preferably from 0.02 to 0.5 weight parts, even more preferably from 0.03 to 0.3 weight parts, even more preferably from 0.05 to 0.25 weight parts, even more preferably from 0.1 to 0.22 weight parts per 100 weight parts of the oil or fat (A) from the standpoints of flavor, external appearance and industrial oil/fat productivity.

When one or more other plant sterols are incorporated in addition to the vegetable-oil-derived sterol, the content of the ingredient (B) may be preferably more than 1.0 weight parts but not more than 4.7 weight parts, more preferably from 1.2 to 4.6 weight parts, even more preferably from 2.0 to 4.5 weight parts, even more preferably from 3.0 to 4.4 weight parts, even more preferably from 3.5 to 4.3 weight parts per 100 weight parts of the oil or fat (A) from the standpoints of flavor, external appearance and industrial oil/fat productivity.

In a still further embodiment of the present invention, the plant sterol (free sterol) may contain a plant stanol (free stanol). Examples of the plant sterol (free sterol) include brassicasterol, isofucosterol, stigmasterol, 7-stigmastenol, α-sitosterol, β-sitosterol, campesterol, brassicastanol, isofucostanol, stigmastanol, 7-stigmastanol, α-sitostanol, β-sitostanol, campestanol, cycloartenol, cholesterol, and avenasterol. Of these plant sterols, brassicasterol, campesterol, stigmasterol and β-sitosterol are preferred from the standpoints of industrial oil/fat productivity and flavor.

In the plant sterol, the total content of brassicasterol, campesterol, stigmasterol and β-sitosterol may be preferably 90% or more, more preferably from 92 to 100%, even more preferably from 94 to 99% from the standpoints of flavor, external appearance, industrial oil/fat productivity, the precipitation of crystals, storage stability at low-temperature, and physiological effects.

The content of brassicasterol in the plant sterol may be preferably from 0.5 to 15%, more preferably from 0.7 to 11%, even more preferably form 3 to 10% from the standpoints of flavor, external appearance, industrial oil/fat productivity, the precipitation of crystals, storage stability at low-temperature, and physiological effects.

The content of campesterol in the plant sterol may be preferably from 10 to 40%, more preferably from 20 to 35%, even more preferably form 23 to 29% from the standpoints of flavor, external appearance, industrial oil/fat productivity, the precipitation of crystals, storage stability at low-temperature, and physiological effects.

The content of stigmasterol in the plant sterol may be preferably from 3 to 30%, more preferably from 11 to 25%, even more preferably form 17 to 24% from the standpoints of flavor, external appearance, industrial oil/fat productivity, the precipitation of crystals, storage stability at low-temperature, and physiological effects.

The content of β-sitosterol in the plant sterol may be preferably from 20 to 60%, more preferably from 30 to 56%, even more preferably form 42 to 51% from the standpoints of flavor, external appearance, industrial oil/fat productivity, the precipitation of crystals, storage stability at low-temperature, and physiological effects.

The content of cholesterol in the plant sterol may be preferably 1% or less, more preferably from 0.01 to 0.8%, even more preferably from 0.1 to 0.7%, even more preferably from 0.2 to 0.6% from the standpoint of the lowering of blood cholesterol and industrial oil/fat productivity.

In a still further embodiment of the present invention, the oil or fat composition contains the plant sterol fatty acid ester (C). The content of the ingredient (C) is from 0.2 to 8 weight parts per 100 weight parts of the oil or fat (A). From the standpoints of flavor and external appearance, however, the content of the ingredient (C) may be preferably from 0.25 to 5 weight parts, more preferably from 0.3 to 3 weight parts, even more preferably from 0.33 to 1 weight parts, even more preferably from 0.35 to 0.5 weight parts. For the inhibition of the formation of conjugated acids, 0.2 weight parts or more are needed. For the retention of good external appearance and solubility, it is needed to limit at 8 weight parts or less.

In a still further embodiment of the present invention, the plant sterol fatty acid ester may contain a plant stanol fatty acid ester. Examples of the plant sterol fatty acid ester include brassicasterol fatty acid esters, isofucosterol fatty acid esters, stigmasterol fatty acid esters, 7-stigmastenol fatty acid esters, α-sitosterol fatty acid esters, β-sitosterol fatty acid esters, campesterol fatty acid esters, brassicastanol fatty acid esters, isofucostanol fatty acid esters, stigmastanol fatty acid esters, 7-stigmastanol fatty acid esters, α-sitostanol fatty acid esters, β-sitostanol fatty acid esters, campestanol fatty acid esters, cycloartenol fatty acid esters, cholesterol fatty acid esters, and avenasterol fatty acid esters. Of these plant sterol fatty acid esters, brassicasterol fatty acid esters, campesterol fatty acid esters, stigmasterol fatty acid esters and β-sitosterol fatty acid esters are preferred from the standpoints of industrial oil/fat productivity and flavor.

In a still further embodiment of the present invention, it is preferred from the standpoints of flavor, external appearance, industrial oil/fat productivity, the precipitation of crystals, storage stability at low-temperature and physiological effects that in the plant sterol fatty acid ester, the total content of brassicasterol fatty acid esters, campesterol fatty acid esters, stigmasterol fatty acid esters and β-sitosterol fatty acid esters and the contents of the respective fatty acid esters are similar to those of the ingredient (B).

In a still further embodiment of the present invention, the content of unsaturated fatty acids in the fatty acids that constitute the plant sterol fatty acid ester (C) may be preferably 80% or more, more preferably from 85 to 100%, even more preferably from 86 to 98%, even more preferably from 88 to 93% from the standpoints of flavor, external appearance, storage stability at low-temperature, the precipitation of crystals, industrial oil/fat productivity, oxidation stability and physiological effects. It is to be noted that from the standpoints of industrial oil/fat productivity and oxidation stability, such unsaturated fatty acids may preferably be different from the fatty acids that constitute the diacylglycerol.

In a still further embodiment of the present invention, the weight ratio of the ingredient (B) to the ingredient (C), (B)/(C), may be preferably 1.3 or less, more preferably from 0.1 to 1.2, even more preferably from 0.2 to 1, even more preferably from 0.3 to 0.8, even more preferably from 0.4 to 0.7 from the standpoints of flavor, external appearance and industrial oil/fat productivity. To achieve such a composition, it is preferred to use an undeodorized oil or fat as a part or the whole part of the oil or fat material and to conduct the hydrolysis step by enzymatic hydrolysis alone or by a combination of enzymatic hydrolysis and high-pressure hydrolysis.

In a still further embodiment of the present invention, the content of water in the oil or fat composition may be preferably 1,300 ppm or less, more preferably from 10 to 1,100 ppm, even more preferably from 100 to 1,000 ppm, even more preferably from 200 to 900 ppm from the standpoints of flavor and low-temperature external appearance.

In a still further embodiment of the present invention, the addition of the ingredients (B) and/or (C) to the ingredient (A) may develop a problem that the water contained in the added ingredients (B) and/or (C) may affect the flavor and low-temperature external appearance. For the avoidance of this problem, it is preferred to lower the content of water in the oil or fat composition according to the present invention by adding the ingredients (B) and/or (C), the water contents of which are already low, to the oil or fat (A) or by conducting heating under reduced pressure to perform a water removal operation subsequent to the addition of the ingredients (B) and/or (C) to the ingredient (A). To inhibit the formation of trans unsaturated fatty acids by further limiting the thermal history, it is also preferred to produce the oil or fat composition according to the present invention by preparing beforehand a composition (master batch) of the ingredient (A) and the ingredients (B) and/or (C) added at high contents, conducting the above-described water removal operation, and then adding the ingredient (A) to dilute the master batch.

In a still further embodiment of the present invention, the temperature at the time of dissolving the ingredients (B) and/or (C) in the ingredient (A) upon preparation of a master batch may be set at preferably from 70 to 160° C., more preferably from 75 to 140° C., even more preferably from 80 to 130° C., even more preferably from 85 to 125° C. from the standpoints of solubility, flavor and cost. In this case, the following four methods ((i) to (iv)) may be exemplified as a preparation method, with the method (i) being preferred. (i) After heating the ingredient (A) beforehand, the ingredients (B) and/or (C) is dissolved. (ii) After separately heating the ingredient (A) and the ingredients (B) and/or (C) beforehand, they are mixed and dissolved together. (iii) After mixing the ingredient (A) and the ingredients (B) and/or (C) together, the mixture is heated to dissolve them together. (iv) After heating the ingredients (B) and/or (C) beforehand, the ingredients (B) and/or (C) are mixed and dissolved in the ingredient (A).

It is preferred from the standpoints of the prevention of precipitation of crystals and oxidation stability to maintain the temperature of the master batch, which has been obtained by conducting the dissolution as described above, until the subsequent deodorization step such that the temperature does not change beyond ±20° C., preferably beyond ±10° C. from the temperature at the time of the dissolution.

In a still further embodiment of the present invention, the contents of the ingredients (B) and (C) in the master batch upon conducting a water removal operation may be preferably from 10 to 50%, more preferably from 12 to 32%, even more preferably from 16 to 28%, even more preferably from 18 to 24%, all in terms of the free plant sterol, from the standpoints of flavor, external appearance and industrial oil/fat productivity. In a still further embodiment of the present invention, the heating temperature at the time of water removal may be set at preferably from 60 to 230° C., more preferably from 70 to 150° C., even more preferably from 80 to 110° C., even more preferably from 85 to 99° C. from the standpoints of external appearance, the inhibition of formation of trans unsaturated fatty acids, and flavor. In this case, it is preferred from the standpoints of the efficiency of water removal and flavor to heat the master batch under reduced pressure while bubbling steam or nitrogen gas.

[Production Example of Oil or Fat Composition]

To an oil or fat (A) (80 weight parts, water content: 800 ppm) which contained an ingredient (C), an ingredient (B) (20 weight parts, water content: 1.5%) is added (the composition of the ingredient (B): brassicasterol, 9%; campesterol, 27%; stigmasterol, 22%; β-sitosterol, 42 wt %). The mixture is heated to 120° C., at which the ingredient (B) is dissolved to produce a master batch. The master batch is then deodorized at 95° C. and 30 torr for 1 hour while bubbling steam. The ingredient (A) is added to the deodorized oil or fat to prepare an oil or fat composition such that the content of the ingredient (B) becomes 4.22% and the content of the ingredient (C) becomes 0.26%. The oil or fat composition obtained as described above has a water content of 800 ppm, and its flavor and low-temperature external appearance are good. A testing method for a low-temperature external appearance is described below.

[Test for Low-Temperature External Appearance]

After aliquots (45 g) of the oil or fat composition are placed and sealed tight in 50-mL glass sample bottles, respectively, they are stored under the following cooling conditions A or B:

Cooling conditions A: Allowed to stand at 5° C. for 4 weeks.

Cooling conditions B: Allowed to stand at 0° C. for 1 day.

Subsequent to the storage, each glass sample bottle was visually observed for the state of precipitation of crystals therein. The clearer the contents, the better the evaluation of low-temperature external appearance.

In a still further embodiment of the present invention, the oil or fat composition may preferably contain an antioxidant (D). From the standpoints of flavor, oxidation stability, coloring and the like, the content of the antioxidant may be from 0.005 to 0.5 weight parts, more preferably from 0.04 to 0.25 weight parts, even more preferably from 0.08 to 0.2 weight parts per 100 parts by weight of the oil or fat (A). As the antioxidant, any antioxidant may be used insofar as it is commonly used in foods. Examples include vitamin E, butylhydroxytoluene (BHT), butylhydroxyanisole (BHA), tert-butylhydroquinone (TBHQ), vitamin C and derivatives thereof, phospholipids, and natural antioxidants such as rosemary extract, among which vitamin E, vitamin C and derivatives thereof are preferred. It is more preferred to use two or more of these antioxidants in combination.

In a still further embodiment of the present invention, α, β, γ or δ-tocopherol or a mixture thereof may be used as vitamin E. Especially from the viewpoint of oxidation stability, δ-tocopherol is preferred. Commercial products of vitamin E include "E-MIX D" and "E-MIX 80" (products of Eisai Co., Ltd.), "MDE-6000" (product of Yashiro Co., Ltd.), and "E-Oil 400" (product of Riken Vitamin Co., Ltd.). In a still further embodiment of the present invention, the content of vitamin E may be preferably from 0.02 to 0.5 weight parts, more preferably from 0.05 to 0.4 weight parts, even more preferably from 0.1 to 0.3 weight parts, even more preferably from 0.18 to 0.25 weight pats, even more preferably from 0.19 to 0.22 weight parts, all in terms of tocopherol per 100 weight parts of the oil or fat (A).

In a still further embodiment of the present invention, as vitamin C and derivatives thereof, those soluble in the oil or fat (A) are preferred. More preferred are higher fatty acid esters, for example, those having $C_{12-22}$ acyl groups. Even more preferred are L-ascorbic acid palmitate and L-ascorbic acid stearate, with L-ascorbic acid palmitate being even more preferred.

In a still further embodiment of the present invention, the content of vitamin C or a derivative thereof may be preferably from 0.004 to 0.1 weight parts, more preferably from 0.006 to 0.08 weight parts, even more preferably from 0.008 to 0.06 weight parts, all in terms of ascorbic acid per 100 weight parts of the oil or fat (A).

When the oil or fat composition according to the present invention is mixed with water or is used in a water-containing food and is stored over a long term or at a light place, it is preferred from the standpoint of preventing any flavor deterioration and the production of any unpleasant taste to make substantially free of any L-ascorbic acid fatty acid ester as an antioxidant and to use vitamin E, preferably δ-tocopherol. The flavor deterioration in the above-described case is totally different from a deterioration occurred on a diacylglycerol-containing oil or fat, which is free of any water phase, upon cooking. In other words, a deterioration of a diacylglycerol-containing oil or fat, which is free of any water phase, upon cooking is attributed to oxidation under heat. On the other hand, a deterioration in flavor after the storage of a food, which contains a diacylglycerol-containing oil phase according to the present invention and water, is attributed to the occurrence of a metallic taste and an unpleasant taste.

When the content of trans unsaturated fatty acids in the oil or fat (A) in a water-containing food exceeds 4% based on the whole fatty acids in the oil or fat (A), a substantial deterioration in flavor tends to take place after long-term storage. In a still further embodiment of the present invention, it is particularly effective for the reduction of a deterioration in the flavor of a food having an oil phase, which contains diacylglycerol of such low trans unsaturated fatty acid content, to make substantially free of any L-ascorbic acid fatty acid ester as an antioxidant and to use vitamin E, preferably δ-tocopherol.

The expression "substantially free" as used herein means that the content of an L-ascorbic acid fatty ester in an oil phase is 15 ppm or less. As the L-ascorbic acid fatty ester, L-ascorbic acid palmitate, L-ascorbic acid stearate or the like may be mentioned. It is preferred to contain δ-tocopherol at 200 ppm or more in a food, because a sufficient effect may be brought about for the reduction of a deterioration in flavor caused by the production of a metallic taste during storage. Depending upon the raw material and/or the production process, the diacylglycerol-containing oil or fat may contain raw-material-derived δ-tocopherol at 50 to 100 ppm in some instances. At this concentration, however, no sufficient effect is available for the reduction of a deterioration in flavor. The content of δ-tocopherol in the food, specifically in its oil phase may be preferably from 250 to 1,200 ppm, more preferably from 300 to 1,000 ppm, even more preferably from 350 to 700 ppm, even more preferably from 400 to 600 ppm.

In a still further embodiment of the present invention, the ratio ($δ/(α+β)$, weight ratio) of the amount of δ-tocopherol to the total amount of α-tocopherol and β-tocopherol in total tocopherol may be preferably more than 2, more preferably from 2.5 to 20, even more preferably from 3 to 10, even more preferably from 4 to 8 from the standpoints of flavor improvements and cost.

In a still further embodiment of the present invention, the weight ratio of oil phase/water phase in a water-containing food may be preferably from 1/99 to 99/1, more preferably from 5/95 to 90/10. It is still more preferred to select a desired ratio depending upon the form of the food. In the case of a food in which a water phase and an oil phase are not emulsified together but are separated from each other as in a separated dressing, the weight ratio of oil phase/water phase may be preferably from 5/95 to 80/20, more preferably from 10/90 to 60/40, even more preferably from 20/80 to 40/60.

In a still further embodiment of the present invention, in the water phase of a water-containing food, it is possible to incorporate, depending upon the objective of the food, one or more of water; edible vinegars such as rice vinegar, sake lees vinegar, apple vinegar, grape vinegar, cereal vinegar, and synthetic vinegar; common salt; seasonings such as sodium glutamate; saccharides such as sugar and starch syrup; taste-imparting substances such as sake, sweet sake and soy sauce; various vitamins; organic acids such as citric acid, and salts thereof; spices; and squeezed juices of various vegetables or fruits, such as lemon juice. To a food according to the present invention, it is also possible to add, as needed, one or more of thickening polysaccharides such as xanthan gum, gellan gum, guar gum, tamarind gum, carageenan, pectin, and tragacanth gum; starches such as potato starch and modified starch and their decomposition products; proteins such as soybean protein, milk protein, egg protein and wheat protein, and their decomposition products and isolated products; emulsifiers such as sugar fatty acid esters, sorbitan fatty acid esters, polyoxyethylene sorbitan fatty acid esters, glycerol fatty acid monoesters, polyglycerol fatty acid esters, polyglycerol condensed ricinoleic acid esters, glycerol organic acid fatty acid esters, propylene glycol fatty acid esters and lecithin, and their enzymolysates; dairy products such as milk; and various phosphate salts.

In a still further embodiment of the present invention, it is preferred to add a crystallization inhibitor (E) further to the oil or fat composition. Examples of the crystallization stabilizer usable in the present invention include polyol fatty acid esters such as polyglycerol condensed ricinoleic acid ester, polyglycerol fatty acid esters, sucrose fatty acid esters, sorbitan fatty acid esters, polyoxyethylene sorbitan fatty acid esters, and propylene glycol fatty acid esters. Preferred are polyglycerol fatty acid esters, sucrose fatty acid esters and sorbitan fatty acid esters, and more preferred are polyglycerol fatty acid esters. The HLB values of such polyol fatty acid esters may be preferably 4 or less, more preferably from 0.1 to 3.5 [as measured by the Griffin's calculation formula, J. Soc. Cosmet. Chem., 1, 311 (1949)].

In a still further embodiment of the present invention, the content of unsaturated fatty acids in fatty acids that constitute a polyglycerol fatty acid ester may be preferably from 50 to 95%, more preferably from 51 to 80%, even more preferably from 52 to 60% from the standpoints of workability and the inhibition of crystallization. From the standpoint of facilitating the dissolution of the polyglycerol fatty acid ester in the oil or fat, it is preferred to control the content of such unsaturated fatty acids at 50% or more. From the standpoint of inhibiting the crystallization of the oil or fat, on the other hand, it is preferred to control the content of such unsaturated fatty acids at 95% or less. The carbon numbers of these unsaturated fatty acids may range preferably from 10 to 24, more preferably from 16 to 22. Specific examples include palmitoleic acid, oleic acid, petroselinic acid, elaidic acid, linoleic acid, linolenic acid, gadoleic acid, and erucic acid, with oleic acid, linoleic acid and gadoleic acid being preferred. The content of oleic acid in the unsaturated fatty acids that constitute the polyglycerol fatty acid ester may be preferably 80% or more, more preferably from 90 to 99.8% from the standpoints of workability, the inhibition of crystallization, and cost. The content of linoleic acid in the constituent unsaturated fatty acids of the polyglycerol fatty acid ester may be preferably 10% or less, more preferably from 0.1 to 5% from the standpoints of workability, the inhibition of crystallization, and cost. The content of gadoleic acid in the constituent unsaturated fatty acids of the polyglycerol fatty acid ester may be preferably 10% or less, more preferably from 0.1 to 5% from the standpoints of workability, the inhibition of crystallization, and cost.

In a still further embodiment of the present invention, the content of saturated fatty acids in the fatty acids that constitute the polyglycerol fatty acid ester may be preferably from 5 to 50%, more preferably from 20 to 49%, even more preferably from 40 to 48% from the standpoints of workability and the inhibition of crystallization. The carbon numbers of these saturated fatty acids may range preferably from 10 to 24, more preferably from 12 to 22. Specific examples include lauric acid, myristic acid, palmitic acid, stearic acid, arachidic acid, and behenic acid, with myristic acid, palmitic acid and stearic acid being preferred. The content of palmitic acid in the saturated fatty acids that constitute the polyglycerol fatty acid ester may be preferably 80% or more, more preferably from 90 to 99.8% from the standpoints of workability, the inhibition of crystallization, and cost. The content of myristic acid in the constituent saturated fatty acids of the polyglycerol fatty acid ester may be preferably 10% or less, more preferably from 0.1 to 5% from the standpoints of workability, the inhibition of crystallization, and cost. The content of stearic acid in the constituent saturated fatty acids of the polyglycerol fatty acid ester may be preferably 10% or less, more preferably from 0.1 to 5% from the standpoints of workability, the inhibition of crystallization, and cost. Further, the weight ratio of palmitic acid to oleic acid (C16:0/C18:1) in the constituent fatty acids may be preferably from 0.6 to 1.2, more preferably from 0.7 to 1.1, even more preferably from 0.8 to 1, even more preferably from 0.8 to 0.9 from the standpoints of workability, the inhibition of crystallization, and cost.

In a still further embodiment of the present invention, the crystallization inhibitor (E) may be a polyglycerol fatty acid ester the degree of esterification of which may be preferably 80% or more, more preferably from 85 to 100%, even more preferably from 90 to 100% from the standpoint of low-temperature resistance. It is to be noted that the term "degree of esterification" as used herein means a value, as expressed in terms of percentage (%), of the number of esterified hydroxyl groups in a molecule of a polyglycerol fatty acid ester based on the number of the entire hydroxyl groups in a molecule of the corresponding polyglycerol. In the polyglycerol fatty acid ester, the average polymerization degree of the corresponding polyglycerol may be preferably from 2 to 30, more preferably from 3 to 20, even more preferably from 3 to 12 from the standpoint of low-temperature resistance. In the present invention, the average polymerization degree of each polyglycerol is calculated from its hydroxyl value. Even more preferably, the content of the unsaturated fatty acids in the fatty acids that constitute the polyglycerol fatty acid ester may be from 52 to 60%, and in the unsaturated fatty acids consisting of oleic acid, linoleic acid and gadoleic acid, the content of oleic acid may be from 90 to 99.8%. Yet even more preferably, the content of the unsaturated fatty acids in the fatty acids that constitute the polyglycerol fatty acid ester may be from 40 to 48%, and in the saturated fatty acids consisting of myristic acid, palmitic acid and stearic acid, the content of palmitic acid may be from 90 to 99.8%. Further, the weight ratio of palmitic acid to oleic acid (C16:0/C18:1) in the fatty acids that constitute the polyglycerol fatty acid ester may preferably be from 0.8 to 0.9.

In a still further embodiment of the present invention, the content of the crystallization inhibitor (E) may be preferably from 0.01 to 2 weight parts, more preferably from 0.02 to 0.5 weight parts, even more preferably from 0.05 to 0.2 weight parts per 100 weight parts of the oil or fat (A) from the standpoints of workability, flavor and the inhibition of crystallization. An illustrative formula making use of a crystallization inhibitor is shown:

Illustrative Formula
Oil or fat (A) 100 weight parts
Plant sterol (B) 4.2 weight parts
Plant sterol fatty acid ester (C) 0.3 weight parts
Crystallization inhibitor (E)*1 0.075 weight parts
*1: Polyglycerol fatty acid ester P (the composition of constituent fatty acids: C14:0, 1.5 wt %; C16:0, 43.9 wt %; C18:0, 1.2 wt %; C18:1, 51.3 wt %; C18:2, 1.9 wt %; C20:1, 0.2 wt %; the degree of esterification: 80% or more).

In a still further embodiment of the present invention, it is preferred to add an organic carboxylic acid of from 2 to 8 carbon number further to the oil or fat composition. The content of the organic carboxylic acid of from 2 to 8 carbon number may be preferably from 0.001 to 0.01 weight parts, more preferably from 0.0012 to 0.007, even more preferably from 0.0015 to 0.0045 weight parts, even more preferably from 0.0025 to 0.0034 weight parts per 100 weight parts of the oil or fat (A) from the standpoints of flavor, external appearance and oxidation stability.

In a still further embodiment of the present invention, the oil or fat composition may be obtained by choosing an oil or fat material and a production process such that the ingredient (A) has the predetermined composition, adding the ingredient (B) and ingredient (C) to give the predetermined proportions, optionally adding the antioxidant (D), the crystallization inhibitor (E), the organic acid (salt) and/or the like, and then heating and stirring the mixture as needed. An antioxidant such as a vitamin C derivative or vitamin E may be added after dissolving it in a solvent beforehand.

The oil or fat composition obtained as described above may be used in various foods, because its use is good from the standpoints of flavor, texture, external appearance, workability and the like.

In a still further embodiment of the present invention, these foods may be oil or fat-containing processed foods containing the oil or fat composition as portions of the foods. Examples of such oil or fat-containing processed foods include health foods, functional foods, specific health foods, medical foods and the like, all of which exhibit specific functions to achieve the promotion of health. Specific products include bakery food products such as breads, cakes, biscuits, pies, pizza crusts, and bakery mixes; oil-in-water emulsified products such as soups, sauces, emulsified dressings, mayonnaises, coffee whiteners, ice creams, and whipped creams; water-in-oil emulsified products such as margarines, spreads, and butter creams; snacks such as potato chips; confectioneries such as chocolates, caramels, candies, and desserts; processed meat foods such as hams, sausages, and hamburger steaks; dairy products such as milks, cheeses, and yogurts; doughs; enrober oils or fats; filling oils or fats; noodles; frozen foods; pouch-packed foods; drinks; roux; and separated dressings. These oil or fat-containing processed foods may each be produced by adding, in addition to the above-described oil or fat composition, one or more food materials which are commonly employed depending upon the kind of the oil or fat-containing processed food. The oil or fat composition according to the present invention may be added generally in a proportion of from 0.1 to 100% to a food, with from 1 to 80% being preferred, although its proportion varies depending upon the kind of the food.

The oil or fat composition according to the present invention may also be used as a cooking oil, specifically as a frying oil, a pan-frying oil, a parting oil or the like. The oil or fat composition may be used in the cooking of deep-fried food products, roasted, broiled, grilled, baked or fried food products, pan-fried food products and the like; the heatless preparation of dressings, mayonnaises, carpaccio and the like; the production of bakery food products such as breads and cakes. As deep-fried food products, it is possible to cook or prepare, for example, delicatessens such as croquettes, tempura (deep-fried fish and vegetables), fried pork cutlets, kara-age (foods fried with coat of flour or starch), fried fish, and egg rolls; snacks such as potato chips, tortilla chips, and fabricated potatoes; fried confectioneries such as fried rice crackers; fried potatoes; fried chicken; donuts; instant noodles; and the like. As roasted, broiled, grilled, baked or fried food products, it is possible to cook or prepare, for example, steaks, hamburger steaks, meuniere, teppan-yaki (meat grilled on a hot plate), piccata, omelet, takoyaki (small balls of pancake-like texture with chopped octopus inside), okonomiyaki (pancake/pizza-like pie with ingredients of desired choice inside), pan-fried noodles (cooked with a special kind of sauce, vegetables, meat, etc.), and the like. As pan-fried food products, it is possible to cook Chinese dishes such as fried rice (cooked with other ingredients such as egg, chopped onion, etc.) and stir-fried vegetables. The oil or fat composition according to the present invention may provide each cooked food or product with a better flavor and external appearance than conventional oils or fats.

When an oil or fat derived from a food material is contained because of the formula of a mix or the like, the weight ratio of the oil or fat derived from the food material to the oil or fat composition according to the present invention may be preferably from 95:5 to 1:99, more preferably from 95:5 to 5:95, even more preferably from 85:15 to 5:95, even more preferably from 40:60 to 5:95.

In a still further embodiment of the present invention, the oil or fat composition may be used in an oil-in-water emulsified composition. The weight ratio of an oil phase to a water phase may be preferably from 1/99 to 90/10, more preferably from 10/90 to 80/20, even more preferably from 30/70 to 75/25, even more preferably from 60/40 to 72/28. An emulsifier may be contained preferably in a proportion of from 0.01 to 5%, with from 0.05 to 3% being particularly preferred. Examples of the emulsifier include various proteins such as egg proteins, soybean proteins, milk proteins, proteins isolated from these proteins, and (partial) hydrolysates of these proteins; sucrose fatty acid esters; sorbitan fatty acid esters; polyoxyethylene sorbitan fatty acid esters; glycerol fatty acid monoesters; polyglycerol fatty acid esters; polyglycerol condensed ricinoleic acid esters; glycerol organic acid fatty acid esters; propylene glycol fatty acid esters; and lecithin and enzymatic hydrolysates thereof. A stabilizer may be contained in a proportion of preferably from 0 to 5%, more preferably from 0.01 to 2%. Examples of the stabilizer include thickening polysaccharides and starches, such as xanthan gum, gellan gum, guar gum, carageenan, pectin, tragacanth gum, and glucomannan (konjakmannan). It is also possible to use one or more taste-imparting substances such as common salt, sugar, vinegar, fruit juices, and seasonings; fragrance additives such as spices and flavors; color additives; preservatives; and the like. Using these materials, oil or fat-containing oil-in-water foods such as mayonnaises, emulsified dressings, coffee whiteners, ice creams, whipped creams and drinks may be prepared by conventional procedure.

In a still further embodiment of the present invention, the oil or fat composition may be used in water-in-oil emulsified composition. The weight ratio of a water phase to an oil phase, water phase/oil phase, may be preferably from 85/15 to 1/99, more preferably from 80/20 to 10/90, even more preferably from 70/30 to 35/65. An emulsifier may be contained in a proportion of preferably from 0.01 to 5%, more preferably from 0.05 to 3%. Examples of the emulsifier include various proteins such as egg proteins, soybean proteins, milk proteins, proteins isolated from these proteins, and (partial) hydrolysates of these proteins; sucrose fatty acid esters; sorbitan fatty acid esters; polyoxyethylene sorbitan fatty acid esters; glycerol fatty acid monoesters; polyglycerol fatty acid esters; polyglycerol condensed ricinoleic acid esters; glycerol organic acid fatty acid esters; propylene glycol fatty acid esters; and lecithin and enzymatic hydrolysates thereof. It is also possible to use one or more of taste-imparting substances such as common salt, sugar, vinegar, fruit juices, and seasonings; fragrance additives such as spices and flavors; stabilizers such as thickening polysaccharides and starches; color additives; preservatives; antioxidants; and the like. Using these materials, oil or fat-containing water-in-oil foods such as margarines, spreads, and butter creams may be prepared by conventional procedure.

The oil or fat composition according to the present invention has excellent physiological effects such as body fat accumulation suppressing effect, visceral fat accumulation suppressing effect, weight-gain suppressing effect, serum triglycerol increase suppressing effect, insulin resistance improving effect, blood sugar level suppressing effect, and HOMA index improving effect. In a still further embodiment of the present invention, the oil or fat composition, owing to the possession of such excellent properties, may be used as medicines in the form of capsules, tablets, a granule, a powder, a liquid, a gel or the like. The medicines may each be produced by adding, depending upon the form, one or more of commonly-employed excipients, disintegrators, binders, lubricants, surfactants, alcohols, water, water-soluble high-molecular substances, sweeteners, corrigents, sour agents and the like in addition to the oil or fat composition. In general, the amount of the oil or fat composition according to the present invention to be added to a medicine may be preferably from 0.1 to 80%, more preferably from 0.2 to 50%, even more preferably from 0.5 to 30% although it differs depending upon the use and form of the medicine. As a dosage, it is preferred to administer from 0.2 to 50 g in terms of the oil or fat composition per day in one to several portions. The period of administration may be preferably 1 month or longer, more preferably 2 months or longer, even more preferably from 3 months to 12 months.

In a still further embodiment of the present invention, the oil or fat composition may also be used in feeds. Examples of the feeds include livestock feeds for cows, pigs, chickens, sheep, horses, goats and the like; small animal feeds for rabbits, rats, mice and the like; fish or shellfish feeds for eels, red breams, young yellowtails, shrimps and the like; and pet foods for dogs, cats, birds, squirrels, chipmunks and the like. In general, the amount of the oil or fat composition according to the present invention to be added to a feed may be preferably from 1 to 30%, more preferably from 1 to 20% although it differs depending upon the use and the like of the feed. The oil or fat composition according to the present invention may be used by substituting for the whole part or a part of the oil or fat in the feed.

The feed may be produced by mixing, in addition to the oil or fat composition, one or more of commonly-employed feed materials such as meats, proteins, cereals, brans, lees, sugars, vegetables, vitamins and minerals.

Examples of the meats include livestock meats or beast meats such as beef, pork, mutton or lamb, rabbit and kangaroo, and byproducts thereof; processed meat products (rendering products of the above-described materials, such as meat balls, meat bone meal and chicken meal); fish and shellfish such as tunas, bonitos, amberjacks, sardines, scallops, turbos and fishmeal; and the like. Examples of the proteins include animal proteins such as milk proteins, e.g., casein and whey, and egg protein; and vegetable proteins such as soybean protein. As the cereals, wheat, barley, rye, milo, corn and the like may be mentioned. As the brans, rice bran, wheat bran and the like may be exemplified. As the lees, soybean cakes can be exemplified. The total content of meats, proteins, cereals, brans and lees in a feed may preferably be from 5 to 93.9%.

As the sugars, glucose, oligosaccharide, sugar, molasses, starches, liquid sugar and the like may be mentioned. A sugar may be contained preferably at from 5 to 80% in a feed. As the vegetables, vegetable extracts and the like may be exemplified. A vegetable may be contained preferably at from 1 to 30% in a feed. Examples of the vitamins include A, B1, B2, D, E, niacin, pantothenic acid, and carotene. One or more vitamins may be contained at from 0.05 to 10% in a feed. Examples of the minerals include calcium, phosphorus, sodium, potassium, iron, magnesium, and zinc. One or more minerals may be contained at 0.05 to 10% in a feed. In addition, it is also possible to include one or more of gelling agents, shape retainers, pH adjusters, seasonings, preservatives, nutrient supplements and the like, which are commonly employed in feeds, as needed.

EXAMPLES

Examples are hereinafter described, although the scope of the present invention shall not be limited to the following Examples.

Production of Oils 1

Test 1

As an oil material, the undeodorized rapeseed oil shown in Table 1 was used. Fifty percent (50%) of the oil material was hydrolyzed by high-pressure hydrolysis to obtain fatty acids. Described specifically, water was added to the oil as much as 50% based on the oil, and high-pressure hydrolysis was conducted at 240° C. and 4 MPa with a residence time of 3 hours. Water was then removed under reduced pressure to obtain rapeseed fatty acids. The remaining 50% of the oil material were hydrolyzed by enzymatic hydrolysis to obtain fatty acids. Described specifically, the enzymatic hydrolysis of the oil was conducted at 40° C. for 15 hours while using "LIPASE AY" (product of Amano Enzyme Inc.). Water was then removed from the oil layer under reduced pressure to obtain rapeseed fatty acids.

The fatty acids obtained by the high-pressure hydrolysis and those obtained by the enzymatic hydrolysis were combined to prepare Fatty acid a. Using immobilized lipase ("LIPOZYME RM IM", product of Novozymes A/S), the Fatty acid a and glycerol were subjected at a molar ratio of 2:1 to esterification at 50° C. for 3 hours while removing water under reduced pressure. Subsequent to the esterification, the immobilized enzyme was separated to obtain an esterified oil.

The esterified oil was refined by distillation under reduced pressure (to eliminate unreacted fatty acids), and an aqueous solution of citric acid was added, followed by mixing. Subsequent to the removal of water under reduced pressure, the concentrate was washed with water. The concentrate was then deodorized at 240° C. under reduced pressure for 1 hour to produce Oil A (diacylglycerol content: 84%).

The trans unsaturated fatty acid content and color of the fatty acid and the trans unsaturated fatty acid content, color and flavor of the produced fatty acid are shown in Table 1. The measurement of the diacylglycerol content was performed by gas chromatography. The measurements of the trans unsaturated fatty acid contents and colors were performed by the methods described above. Further, the evaluation of the flavor was organoleptically performed in accordance with the following standards.

A: Good flavor
B: A little inferior flavor
C: Inferior flavor

Test 2

Using, as 50% of an oil material, the undeodorized rapeseed oil shown in Table 1, hydrolysis was conducted by a similar method as the high-pressure hydrolysis described in Test 1 to obtain rapeseed fatty acids. Using, as the remaining 50% of the oil material, the deodorized rapeseed oil shown in Table 1, hydrolysis was conducted by a similar method as the enzymatic hydrolysis described in Test 1 to obtain rapeseed fatty acids.

The fatty acids obtained by the high-pressure hydrolysis and those obtained by the enzymatic hydrolysis were combined to obtain Fatty acid b. From the Fatty acid b and glycerol, Oil B (diacylglycerol content: 85%) was then produced by conducting esterification and post treatment in a similar manner as in Test 1.

Test 3

Using, as an oil material, the deodorized rapeseed oil shown in Table 1, its entirety was hydrolyzed by high-pressure hydrolysis in a similar manner as in Test 1 to obtain Fatty acid c. From the Fatty acid c and glycerol, Oil C (diacylglycerol content: 86%) was then produced by conducting esterification and post treatment in a similar manner as in Test 1.

Test 4

Using, as an oil material, the deodorized rapeseed oil shown in Table 1, 50% of the oil material was hydrolyzed by a similar method as the high-pressure hydrolysis described in Test 1 to obtain rapeseed fatty acids. The remaining 50% of the oil material was hydrolyzed by a similar method as the enzymatic hydrolysis described in Test 1 to obtain rapeseed fatty acids.

The fatty acids obtained by the high-pressure hydrolysis and those obtained by the enzymatic hydrolysis were combined to obtain Fatty acid d. Using the Fatty acid d and glycerol, esterification and post treatment were then conducted in a similar manner as in Test 1 to produce glycerol as glycerol Oil D (diacylglycerol content: 85%).

Test 5

Using, as an oil material, the deodorized rapeseed oil shown in Table 1, its entirety was hydrolyzed by a similar method as the enzymatic hydrolysis described in Test 1 to obtain Fatty acid e. Using the Fatty acid e and glycerol, esterification and post treatment were then conducted in a similar manner as in Test 1 to produce Oil E (diacylglycerol content: 85%).

Test 6

Using, as an oil material, the undeodorized rapeseed oil shown in Table 1, its entirety was hydrolyzed by a similar method as the enzymatic hydrolysis described in Test 1 to obtain Fatty acid f. Using the Fatty acid f and glycerol, esterification and post treatment were then conducted in a similar manner as in Test 1 to produce Oil F (diacylglycerol content: 84%).

TABLE 1

|  | Trans acids (wt %) | Color C (10 R + Y) | Flavor |
|---|---|---|---|
| Undeodorized rapeseed oil | 0.1 | 72 | — |
| Deodorized rapeseed oil | 2.4 | 12 | — |
| Fatty acid a | 1.2 | 47 | — |
| Oil A | 2.2 | 30 | A |
| Fatty acid b | 2.3 | 23 | — |
| Oil B | 3.1 | 20 | A |
| Fatty acid c | 3.9 | 20 | — |
| Oil C | 4.8 | 18 | A |

TABLE 1-continued

|  | Trans acids (wt %) | Color C (10 R + Y) | Flavor |
|---|---|---|---|
| Fatty acid d | 3.2 | 21 | — |
| Oil D | 4.2 | 19 | A |
| Fatty acid e | 2.5 | 22 | — |
| Oil E | 3.6 | 20 | B |
| Fatty acid f | 0.2 | 70 | — |
| Oil F | 1.4 | 35 | B |

The Fatty acids c, d, e, all of which had been obtained by using and hydrolyzing the deodorized oil as an oil material, and the Oils C, D, E, which had been obtained by using and esterifying the fatty acids, respectively, had high trans unsaturated fatty acid content. In particular, the Fatty acid c, which had been obtained by hydrolyzing the whole oil material in accordance with the high-pressure hydrolysis, and the Oil C, which had been obtained by using and esterifying the fatty acid, were significantly high in the trans unsaturated fatty acid content. Further, the Fatty acids e, f, which had been obtained by hydrolyzing the whole oil materials by the enzymatic hydrolysis, and the Oils E, F, which had been obtained by using and esterifying the fatty acids, respectively, were lowered in the trans unsaturated fatty acid content, but were slightly inferior in flavor.

On the other hand, the Fatty acids a, b, which had been obtained by hydrolyzing the oil material in accordance with the combination of the high-pressure hydrolysis and enzymatic hydrolysis, and the Oils A, B, which had been obtained by using and esterifying the fatty acids, respectively, were low in the trans unsaturated fatty acid content, were high in color balance, and were high in quality as fatty acids and oils.

Production 2 of Oils

Example 1

Oils G and H

As an oil material, an undeodorized soybean oil and deodorized rapeseed oil were used. The undeodorized soybean oil was subjected to high-pressure hydrolysis with water as much as 50% based on the oil at 250° C. and 5 MPa with a residence time of 3 hours. Water was then removed under reduced pressure to obtain soybean fatty acids. Wintering was then conducted to lower the saturated fatty acid content so that soybean fatty acids (unsaturated fraction) were produced. The deodorized rapeseed oil was subjected to enzymatic hydrolysis with "LIPASE AY" (product of Amano Enzyme Inc.) at 40° C. for 15 hours. Water was then removed from the oil layer under reduced pressure to obtain rapeseed fatty acids.

The fatty acids obtained by the high-pressure hydrolysis and those obtained by the enzymatic hydrolysis were combined to prepare Fatty acid g. Using immobilized lipase ("LIPOZYME RM IM", product of Novozymes A/S), the Fatty acid g and glycerol were subjected at a molar ratio of 2:1 to esterification at 50° C. for 3 hours while removing water under reduced pressure. The immobilized enzyme was separated to obtain an esterified oil.

The esterified oil was refined by distillation under reduced pressure (to eliminate unreacted fatty acids), and an aqueous solution of citric acid was added, followed by mixing. Subsequent to the removal of water under reduced pressure, the concentrate was washed with water. The concentrate was then deodorized at 240° C. under reduced pressure for 1 hour, followed by the addition of tocopherol to Oil G.

Further, a plant sterol was added to the Oil G to produce Oil H.

Comparative Example 1

Oils I and J

As an oil material, a deodorized soybean oil and deodorized rapeseed oil were used. The deodorized rapeseed oil was hydrolyzed in a similar manner as the high-pressure hydrolysis described in the production process of the Oil G to obtain rapeseed fatty acids.

After the deodorized soybean oil was hydrolyzed by a similar method as the high-pressure dialysis described in the production process of the Oil G, wintering was conducted to lower the saturated fatty acid content so that soybean fatty acids (unsaturated fraction) were produced.

The rapeseed fatty acids and soybean fatty acids obtained as described above were combined to prepare mixed Fatty acid i. Esterification and post treatment were then conducted in a similar manner as in the Oil G, followed by the addition of tocopherol to produce Oil I.

Further, a plant sterol was added to the Oil I to produce Oil J.

An analysis was performed on the Oils G to J. The results are shown in Table 2. It is to be noted that a commercial salad oil was referred to as "Oil K".

[Analytical Methods]

(i) Composition of Glycerides

A sample (10 mg) and a trimethylsilylating agent ("SILYLATING AGENT TH", product of Kanto Chemical Co., Inc.; 0.5 mL) were placed in a glass sample bottle. After tightly sealing, the contents were heated at 70° C. for 15 minutes. The contents were subjected to gas chromatography (GLC) to analyze the composition of glycerides.

GLC Conditions
    System: "MODEL 6890" (manufactured by Hewlett Packard Company)
    Column: "DB-1HT" (manufactured by J&W Scientific Industries, Inc.), 7 m
    Column temperature: Initial, 80° C.; final, 340° C.
    Ramp rate: 10° C./min, held at 340° C. for 20 min.
    Detector: FID, temperature: 350° C.
    Injection port: Split ratio: 50/1, temperature: 320° C.
    Sample injection volume: 1 µL
    Carrier gas: Helium, flow rate: 1.0 mL/min (ii) Composition of Constituent Fatty Acid Following "Method of Preparing Fatty Acid Methyl Esters (2.4.1.2-1996)" in "Standard Methods for the Analysis of Fats, Oils, and Related Materials" (compiled by The Japan Oil Chemists' Society), fatty acid methyl esters were prepared. The thus-obtained sample was subjected to GLC to perform its analysis (American Oil Chem. Soc. Official Method: Celf-96, 2002).

(iii) Plant Sterol, and its Fatty Acid Esters

An analysis was performed in a similar manner as in the analysis of the composition of glycerol.

(iv) Tocopherol

An analysis was performed following "Tocopherol (2.4.10-1996)" in "Standard Methods for the Analysis of Fats, Oils, and Related Materials" (compiled by The Japan Oil Chemists' Society).

TABLE 2

|  | Example of present invention Oil G | Comparative product Oil I | Example of present invention Oil H | Comparative product Oil J |
|---|---|---|---|---|
| Composition of glycerides, wt % | | | | |
| TG | 14.3 | 14.3 | 14.3 | 14.3 |
| DG | 85.2 | 85.1 | 85.2 | 85.1 |
| 1,3 DG | 57.7 | 57.6 | 57.7 | 57.6 |
| MG | 0.5 | 0.6 | 0.5 | 0.6 |
| FFA | 0.1 | 0.1 | 0.1 | 0.1 |
| Composition of constituent fatty acids, wt % | | | | |
| C16:0 | 3.0 | 3.1 | 3.0 | 3.1 |
| C18:0 | 1.2 | 1.2 | 1.2 | 1.2 |
| C18:1 cis | 38.2 | 40.0 | 38.2 | 40.0 |
| trans | 0.1 | 0.1 | 0.1 | 0.1 |
| C18:2 cis | 47.4 | 44.2 | 47.4 | 44.2 |
| trans | 1.2 | 2.2 | 1.2 | 2.2 |
| C18:3 cis | 5.7 | 4.4 | 5.7 | 4.4 |
| trans | 2.2 | 3.7 | 2.2 | 3.7 |
| C20:1 cis | 0.6 | 0.7 | 0.6 | 0.7 |
| Others | 0.4 | 0.4 | 0.4 | 0.4 |
| Total trans UFA | 3.5 | 6.0 | 3.5 | 6.0 |
| Conjugated UFA, wt % | | | | |
| Diene | 0.67 | 1.03 | 0.67 | 1.03 |
| Triene | 0.01 | 0.02 | 0.01 | 0.02 |
| Tetraene | 0 | 0 | 0 | 0 |
| Pentaene | 0 | 0 | 0 | 0 |
| Total conjugated UFA | 0.68 | 1.05 | 0.68 | 1.05 |
| Content of free plant sterol, wt % | 0.22 | 0.26 | 4.22 | 4.26 |
| Content of plant sterol fatty acid esters, wt % | 0.39 | 0.18 | 0.39 | 0.18 |
| Composition of plant sterol, in terms of free forms, wt % | | | | |
| Brassicasterol | 0.03 | 0.03 | 0.30 | 0.36 |
| Campesterol | 0.13 | 0.08 | 1.29 | 0.97 |
| Stigmasterol | 0.04 | 0.03 | 0.39 | 0.36 |
| β-sitosterol | 0.25 | 0.22 | 2.47 | 2.67 |
| Total tocopherol, ppm | 1935 | 1793 | 1935 | 1793 |
| Alpha | 278 | 244 | 278 | 244 |
| Beta | 59 | 33 | 59 | 33 |
| Gamma | 1255 | 1156 | 1255 | 1156 |
| Delta | 344 | 360 | 344 | 360 |

Example 2

Storage Test

The Oils G to J (30 g, each) were placed in glass sample containers for the Lovibond test (depth 1.6 cm×width 13.3 cm×height 3.7 cm), respectively (at that time, the depth of each oil was 1.6 cm). The glass sample containers were allowed to stand at 20° C. for 48 hours under exposure conditions of 2,000 lux fluorescent lamps to perform a storage test. With respect to each oil before and after the storage, its flavor and peroxide value were evaluated.

<Evaluation of Oils>

Organoleptic evaluations were performed in accordance with the below-described ranking standards, and peroxide values (POV) were also measured. The measurement of each POV conducted following "Peroxide Values (2.5.2.1-1996)" in "Standard Methods for the Analysis of Fats, Oils, and Related Materials" (compiled by The Japan Chemists' Society). The results are shown in Table 3.

Flavor of Oil
4: Good (A fresh oil flavor is smelled.)
3: Fair (A fresh oil flavor, grassy smell and bean flavor are slightly felt.)
2: Slightly poor (A grassy smell and bean flavor are strong, and a slightly sharp smell is felt.)
1: Poor (A strong smell is felt with a heavy sensation.)

TABLE 3

| Oils | | Example of present invention Oil G | Comparative product Oil I | Example of present invention Oil H | Comparative product Oil J |
|---|---|---|---|---|---|
| Flavor | Before storage | 4 | 4 | 4 | 3 to 4 |
|  | After storage | 3 | 1 to 2 | 3 to 4 | 3 |
| POV | Before storage | 0.2 | 0.1 | 0.1 | 0.1 |
|  | After storage | 2.7 | 2.7 | 2.2 | 2.2 |

The Oils G and H, examples of the present invention, were found to have a better flavor than the Oils I and J, comparative products, even after storage under severe exposure conditions. They were, however, equivalent in POV.

Example 3

Cooking Test 1

Using each of the Oils G, I and K, fried rice was cooked by the below-described cooking procedure. The oil (10 g) was poured into a frying pan of 24 cm diameter. The frying pan was put over a fire, and the flow rate of town gas was set at 4.0 L/min. Thirty seconds later, "GOHAN" (vacuum-packed pre-cooked rice, product of Toyo Suisan Kaisha, Ltd.) which had been heated at 550 W for 2 minutes in a microwave oven was placed in the frying pan, and was then stir-fried for 120 seconds while breaking up the rice into grain pieces with a wooden spatula. Common salt (1 g) was then added, followed by stir-frying for further 30 seconds. The frying pan was taken off from the fire, and the fried rice was served on a plate.

The flavor and color of the resultant fried rice were organoleptically evaluated in accordance with the below-described standards, respectively. The results are shown in Table 4.

Flavor
4: Good (An inherent rice flavor is smelled with a strong aroma of cooked rice served in a wooden rice bowl.)
3: Fair (A rice flavor is slightly smelled with a slightly strong aroma of cooked rice served in a wooden rice bowl.)
2: Slightly poor (A rice flavor is slightly masked with an oil smell.)
1: Poor (A rice flavor is masked with an oil smell.)

Color
4: Good (Rice is white and shiny.)
3: Fair (Rice is a little white and slightly shiny.)
2: Slightly poor (Rice is a little yellowish, somewhat lacks shininess, and looks slightly dark.)
1: Poor (Rice is yellowish, lacks shininess, and looks dark.)

TABLE 4

| Fried rice | Example of present invention Oil G | Comparative products | |
|---|---|---|---|
| | | Oil I | Oil K |
| Flavor | 4 | 3 | 1 |
| Color | 4 | 3 | 3 |

The fried rice cooked with the Oil G, an example of the present invention, was found to be better in the flavor and color of the cooked food than those cooked with the Oils I and K, comparative products.

Example 4

Cooking Test 2

Using each of the samples of the Oils G to J before and after the storage in Example 2 and the Oil K, a scrambled egg was prepared by the below-described cooking procedure. The oil (14 g) was poured into a frying pan of 24 cm diameter. The frying pan was put over a fire, and the flow rate of town gas was set at 5.0 L/min. Sixty seconds later, common salt (1 g) and pepper (0.2 g) were added to a whole egg (500 g), and then, the egg was beaten with cooking chopsticks. The beaten egg (100 g) was poured into the frying pan, and the frying pan was held for 15 seconds over the fire. After the egg was thoroughly stirred for 15 seconds with the cooking chopsticks, the frying pan was taken off from the fire and the scrambled egg was served on a plate. The flavor and color of the resultant scrambled egg was organoleptically evaluated in accordance with the below-described standards, respectively. The results are shown in Table 5.

Color
  4: Good (Have a bright deep yellow color, and is shiny.)
  3: Fair (Have a somewhat bright yellow color, and is slightly shiny.)
  2: Slightly poor (Have a slightly dull, somewhat dark yellow color.)
  1: Poor (Have a dull and dark color.)
Flavor
  4: Good (An inherent egg flavor is smelled with a rich taste.)
  3: Fair (An inherent egg flavor is smelled a little with a somewhat rich taste.)
  2: Slightly poor (An unpleasant smell of deteriorated oil is felt a little, and an egg flavor is slightly masked.)
  1: Poor (An unpleasant smell of deteriorated oil is felt, and an egg flavor is masked.)

The scrambled eggs cooked with the Oils G and H, example of the present invention, were found to be superior in flavor and color to those cooked with the Oils I, J and K, comparative products. The scrambled eggs cooked with the examples of the invention products were found to be better in flavor and color than those cooked with the comparative products even after storage under severe light exposure conditions.

TABLE 5

| Scrambled eggs | | Example of present invention Oil G | Comparative product Oil I | Example of present invention Oil H | Comparative product Oil J | Comparative product Oil K |
|---|---|---|---|---|---|---|
| Flavor | Before storage | 4 | 3 | 4 | 3 | 1 |
| | After storage | 3 | 2 | 3 | 1 to 2 | — |
| Color | Before storage | 4 | 3 | 4 | 4 | 3 |
| | After storage | 3 | 2 | 3 | 2 to 3 | — |

Example 5

Low-Temperature Resistance

The Oil G with a polyglycerol fatty acid ester P dissolved as a crystallization inhibitor therein was provided as a test sample 1, while the Oil G with a polyglycerol fatty acid ester Q dissolved as a crystallization inhibitor therein was provided as a test sample 2. After those test samples were allowed to stand at 20° C. for 24 hours, they were left over at 0° C. (for 3 days), and the external appearances of the oils were visually observed. The results are shown in Table 6.

TABLE 6

| Low-temperature resistance | | Test sample 1[*1] | Test sample 2[*2] |
|---|---|---|---|
| External appearances of oils | 3 days later | Clear. Formation of crystals was not observed. | Clear. Formation of crystals was not observed. |

[*1] To the Oil G, 0.075 wt % of the polyglycerol fatty acid ester P was added. Constituent fatty acid composition: C14:0, 1.5 wt %; C16:0, 43.9 wt %; C18:0, 1.2 wt %; C18:1, 51.3 wt %; C18:2, 1.9 wt %; C20:1, 0.2 wt %. Degree of esterification: ≧80%.
[*2] To the Oil G, 0.075 wt % of the polyglycerol fatty acid ester Q was added. Constituent fatty acid composition: C14:0, 1.6 wt %; C16:0, 52.6 wt %; C18:0, 0.9 wt %; C18:1, 43.3 wt %; C18:2, 1.4 wt %; C20:1, 0.2 wt %. Degree of esterification: >80%.

The oil with the polyglycerol fatty acid ester P or Q added therein was good in low-temperature resistance at 0° C.

Example 6

Oil phase ingredients, which made use of the diacylglycerol-containing oil described in Table 7, and a water phase were mixed to produce dressings, respectively. The resultant dressings were stored at 50° C. for 4 weeks, and their flavors were then evaluated by the below-described method. The results are shown in Table 8.
[Evaluation Method of Flavor]
  Lettuce was mixed with each of the stored dressings, and was then tasted. The degree of deterioration in taste was evaluated by an evaluation panel of four experts in 10 stages in accordance with the below-described standards, and an average score was determined.
  Ranking standards (compared with the corresponding sample stored at 5° C. and remained free of any deterioration during storage): 10: no difference in taste, 9: a slight deterioration is felt? although it is subtle, 8: a slight deterioration is recognized, 7: a little deterioration is recognized, 6: a deterioration is recognized, 5: A deterioration is clearly recognized, 4: Clearly deteriorated, 3: A rather substantial deterioration is recognized, 2: A substantial deterioration is recognized, 1: Deterioration is considerable.

TABLE 7

| Composition of glycerides (wt %) | |
| --- | --- |
| TG | 13.2 |
| DG | 85.9 |
| MG | 0.8 |
| FFA | 0.1 |
| Composition of fatty acids (wt %) | |
| C16:0 | 3.1 |
| C18:0 | 1.1 |
| C18:1 | 39.1 |

TABLE 7-continued

| | |
| --- | --- |
| C18:2 | 45.3 |
| C18:3 | 4.9 |
| Total trans UFA | 3.5 |
| Total conjugated UFA | 0.68 |
| Plant sterol content (wt %) | |
| Free sterol | 0.68 |
| Fatty acid esters | 0.39 |

TABLE 8

| | Oil phases | | Oil phase/ water phase ratio | Flavor evaluation (10-stage organoleptic evaluation) | |
| --- | --- | --- | --- | --- | --- |
| No. | Kind of oil | Additive(s) | (weight ratio) | Initial | After being stored at 50° C. for 4 weeks |
| 0 | Table 7 | VCP[#1] (250 ppm) | 100/0 | 10 | 8 |
| 1 | Table 7 | VCP (250 ppm) Toc[#2] (2000 ppm) | 30/70 | 10 | 1 Unpleasant taste (metallic taste) |
| 2 | Table 7 | VCP (250 ppm) | 30/70 | 10 | 1 Unpleasant taste (metallic taste) |
| 3 | Table 7 | No additive | 30/70 | 10 | 9 |

[#1]L-ascorbic acid palmitate
[#2]Tocopherol having a δ-Toc content of from 20 to 55 wt %.

As is evident from Table 8, among the foods each of which contained the diacylglycerol-containing oil and the water phase, the comparative products (Nos. 1 and 2) contained L-ascorbic acid fatty acid esters and produced an unpleasant taste (metallic taste) during storage. In contrast, No. 3, an invention example, was reduced in flavor deterioration and hence led to remarkable improvement in its flavor.

Example 7

Oil phase ingredients described in Table 9 and a water phase were mixed to produce dressings, respectively. The resultant dressings were stored for 15 days at room temperature under 2,000 lux fluorescence lamps (720,000 lux hr), and their flavors were then evaluated by a similar method as in Example 7. The results are shown in Table 9.

TABLE 9

| | Oil phases | | Toc content in oil phase | | Oil phase/water phase ratio | Flavor evaluation[*3] | |
| --- | --- | --- | --- | --- | --- | --- | --- |
| No. | Kind of oil | Additive | δ-Toc[*2] (ppm) | δ/(α + β) | (weight ratio) | Initial | After being stored for 15 days under fluorescent lamps |
| 4 | Table 7 | No additive | 128 | 0.9 | 30/70 | 10 | 4 Strong taste of deterioration |
| 5 | Table 7 | Toc (200 ppm)[*1] | 281 | 2.2 | 30/70 | 10 | 5 |
| 6 | Table 7 | Toc (300 ppm)[*1] | 410 | 2.8 | 30/70 | 10 | 7 |
| 7 | Table 7 | Toc (350 ppm)[*1] | 397 | 3.3 | 30/70 | 10 | 6 |
| 8 | Table 7 | Toc (500 ppm)[*1] | 594 | 4.4 | 30/70 | 10 | 7 |

[*1]Tocopherol having a δ-Toc content of from 87 to 98 wt %
[*2]Found (by HPLC method)
[*3]10-Stage organoleptic evaluation From Table 9, Nos. 5 to 8, examples of the present invention, were found to be reduced in flavor deterioration and the occurrence of an unpleasant taste during long-term storage under fluorescent lamps and hence, to be improved in flavor.

The invention claimed is:

1. A method of producing an oil or fat, said method comprising:
   hydrolyzing a first portion of an oil or fat material by a high-pressure hydrolysis method to obtain a first portion of fatty acids;
   hydrolyzing a second portion of an oil or fat material by an enzymatic hydrolysis method to obtain a second portion of fatty acids;
   mixing said first portion of fatty acids and said second portion of fatty acids to obtain a fatty acids material; and
   esterifying said fatty acids material to produce an oil or fat comprising 35 to 95 wt % of diacylglycerols.

2. The method according to claim 1, wherein said hydrolyzing by said high-pressure hydrolysis method comprises hydrolyzing for from 2 to 6 hours with high-pressure hot water having a temperature of from 220 to 270° C.

3. The method according to claim 1, wherein said hydrolyzing by the enzymatic hydrolysis method comprises hydrolyzing with lipase.

4. The method according to claim 1, wherein said esterifying comprises esterifying by lipase.

5. The method according to claim 1, wherein said oil or fat material has a content of trans unsaturated fatty acids of 1 wt % or less.

6. The method according to claim 1, wherein 35 to 95 wt % of said oil or fat material is hydrolyzed by said high-pressure hydrolysis method.

7. The method according to claim 1, wherein said oil or fat has a color measured in accordance with American Oil Chemists' Society Official Method Cc 13e-92 of 30 or less.

8. The method according to claim 1, further comprising deodorizating said oil or fat comprising 35 to 95 wt % diacylglycerols for a time of from 2 minutes to 2 hours at a temperature of from 200 to 280° C. and under a pressure of from 0.01 to 5 kPa.

9. A method of producing oil or fat, said method comprising:
hydrolyzing 35 to 95 wt % of an oil or fat material for a time of from 2 to 6 hours with high-pressure hot water having a temperature of from 220 to 270° C. to obtain a first portion of fatty acids;
hydrolyzing the remainder of said oil or fat material with lipase to obtain a second portion of fatty acids;
mixing said first portion of fatty acids and said second portion of fatty acids to obtain a fatty acids material; and
esterifying said fatty acids material with lipase to produce an oil or fat comprising 35 wt % or more of diacylglycerols.

10. The method according to claim 9, wherein said oil or fat material has a content of trans unsaturated fatty acids of the is 1 wt % or less.

11. The method according to claim 9, wherein said oil or fat has a color measured in accordance with American Oil Chemists' Society Official Method Cc 13e-92 of 30 or less.

12. The method according to claim 9, further comprising deodorizating said oil or fat comprising 35 to 95 wt % diacylglycerols for a time of from 2 minutes to 2 hours at a temperature of from 200 to 280° C. and under a pressure of from 0.01 to 5 kPa.

13. A method of producing oil or fat, said method comprising:
hydrolyzing 35 to 95 wt % of an oil or fat material for a time of from 2 to 6 hours with high-pressure hot water having a temperature of from 220 to 270° C. to obtain a first portion of fatty acids;
hydrolyzing the remainder of said oil or fat material with lipase to obtain a second portion of fatty acids;
mixing said first portion of fatty acids and said second portion of fatty acids to obtain a fatty acids material; and
esterifying said fatty acids material with lipase to produce an oil or fat comprising 35 wt % or more of diacylglycerols, wherein constituent fatty acids of said oil or fat have a content of unsaturated fatty acids of 80 wt % or more, and wherein in all the fatty acids that constitute said oil or fat, the content of conjugated unsaturated fatty acids is 1 wt % or less and the content of trans unsaturated fatty acids is 0.1 to 3.5 wt %.

14. The method according to claim 13, wherein said oil or fat material has a content of trans unsaturated fatty acids of 1 wt % or less.

15. The method according to claim 13, wherein said oil or fat has a color measured in accordance with American Oil Chemists' Society Official Method Cc 13e-92 of 30 or less.

16. The method according to claim 13, further comprising deodorizating said oil or fat comprising 35 to 95 wt % diacylglycerols for a time of from 2 minutes to 2 hours at a temperature of from 200 to 280° C. and under a pressure of from 0.01 to 5 kPa.

* * * * *

UNITED STATES PATENT AND TRADEMARK OFFICE
CERTIFICATE OF CORRECTION

PATENT NO. : 8,524,309 B2  Page 1 of 1
APPLICATION NO. : 13/724373
DATED : September 3, 2013
INVENTOR(S) : Jun Kohori et al.

It is certified that error appears in the above-identified patent and that said Letters Patent is hereby corrected as shown below:

In the Claims:

Col. 29, line 4, "280°C." should read --280°C--

Col. 29, line 10, "270°C." should read --270°C--

Col. 29, line 28, "280°C." should read --280°C--

Col. 29, line 29, "280°C." should read --280°C--

Col. 30, line 5, "270°C." should read --270°C--

Signed and Sealed this
Twenty-sixth Day of November, 2013

Margaret A. Focarino
*Commissioner for Patents of the United States Patent and Trademark Office*